US012807521B2

(12) United States Patent
Ogawa et al.

(10) Patent No.: US 12,807,521 B2
(45) Date of Patent: Nov. 24, 2026

(54) DIALYSIS SOLUTION REGENERATION METHOD

(71) Applicant: TORAY INDUSTRIES, INC., Tokyo (JP)

(72) Inventors: Kumiko Ogawa, Shiga (JP); Harutoki Shimura, Shiga (JP); Shigehisa Hanada, Shiga (JP)

(73) Assignee: TORAY INDUSTRIES, INC., Tokyo (JP)

( * ) Notice: Subject to any disclaimer, the term of this patent is extended or adjusted under 35 U.S.C. 154(b) by 683 days.

(21) Appl. No.: 17/606,266

(22) PCT Filed: Apr. 24, 2020

(86) PCT No.: PCT/JP2020/017821
§ 371 (c)(1),
(2) Date: Oct. 25, 2021

(87) PCT Pub. No.: WO2020/218571
PCT Pub. Date: Oct. 29, 2020

(65) Prior Publication Data
US 2022/0212962 A1 Jul. 7, 2022

(30) Foreign Application Priority Data
Apr. 26, 2019 (JP) ................................ 2019-085295
Apr. 26, 2019 (JP) ................................ 2019-085296

(51) Int. Cl.
*C02F 1/44* (2023.01)
*A61M 1/16* (2006.01)
(Continued)

(52) U.S. Cl.
CPC .......... *C02F 1/441* (2013.01); *A61M 1/1696* (2013.01); *B01D 61/025* (2013.01);
(Continued)

(58) Field of Classification Search
CPC . C02F 1/441; B01D 71/56; B01D 61/02–029; A61M 1/16–1698
See application file for complete search history.

(56) References Cited

U.S. PATENT DOCUMENTS 5,238,613 A * 8/1993 Anderson ............. B01D 69/02 264/425
2003/0094406 A1* 5/2003 Smith ................. B01D 65/022 210/96.2

(Continued)

FOREIGN PATENT DOCUMENTS

CN 108472800 A 8/2018
EP 1 857 439 A1 11/2007

(Continued)

OTHER PUBLICATIONS

Environmental Colloids and Particles: Behaviour, Separation and Characterisation, vol. 10, 2207, Chapter 4. Ultrafiltration and its Applications to Sampling and Characterisation of Aquatic Colloids (Year: 2007).*

(Continued)

*Primary Examiner* — Richard C Gurtowski
*Assistant Examiner* — Marriah C G Ellington
(74) *Attorney, Agent, or Firm* — Birch, Stewart, Kolasch & Birch, LLP

(57) ABSTRACT

The present invention relates to a dialysate regeneration method that reduces a urea concentration of a urea-containing aqueous solution, the method including a reverse osmosis process of obtaining, from the urea-containing aqueous solution, a concentrate having a higher urea concentration and a permeate having a lower urea concentration by using a reverse osmosis membrane element at an operating pressure of 0.5 MPa or more and 2.0 MPa or less, in which the urea concentration of the urea-containing aqueous solution is 0.5 g/L or more, the reverse osmosis membrane element (Continued)

includes a reverse osmosis membrane, and the reverse osmosis membrane has a pore diameter of 7.0 Å or less as measured by a positron annihilation lifetime measurement method.

12 Claims, 4 Drawing Sheets

(51) Int. Cl.

| | |
|---|---|
| ***B01D 61/02*** | (2006.01) |
| ***B01D 69/02*** | (2006.01) |
| ***B01D 69/10*** | (2006.01) |
| ***B01D 71/56*** | (2006.01) |
| ***C02F 1/42*** | (2023.01) |
| ***C02F 101/38*** | (2006.01) |

(52) U.S. Cl.
CPC ........... *B01D 61/026* (2022.08); *B01D 69/02* (2013.01); *B01D 69/107* (2022.08); *B01D 71/56* (2013.01); *C02F 1/42* (2013.01); *B01D 2311/2623* (2013.01); *B01D 2317/025* (2013.01); *B01D 2325/06* (2013.01); *C02F 2101/38* (2013.01); *C02F 2301/08* (2013.01)

(56) References Cited

U.S. PATENT DOCUMENTS

| | | | | |
|---|---|---|---|---|
| 2009/0050563 | A1* | 2/2009 | Ruehr | B01D 65/08 210/636 |
| 2010/0006495 | A1* | 1/2010 | Buschmann | B01D 71/56 210/500.28 |
| 2012/0067822 | A1* | 3/2012 | Ujang | B01D 69/02 210/651 |
| 2014/0076728 | A1* | 3/2014 | Prakash | B01D 61/12 204/627 |
| 2014/0217025 | A1 | 8/2014 | Sandford | |
| 2014/0217028 | A1 | 8/2014 | Pudil et al. | |
| 2015/0190759 | A1* | 7/2015 | Shimura | B01D 67/00165 210/500.38 |
| 2015/0283515 | A1 | 10/2015 | Koiwa et al. | |
| 2015/0352270 | A1 | 12/2015 | Pudil et al. | |
| 2016/0106902 | A1 | 4/2016 | Sandford | |
| 2016/0354727 | A1* | 12/2016 | Denvir | B01D 61/025 |
| 2016/0375190 | A1 | 12/2016 | Blatter et al. | |
| 2017/0065762 | A1* | 3/2017 | Larsen | B01D 61/0022 |
| 2017/0368510 | A1* | 12/2017 | Tanaka | B01D 71/56 |
| 2019/0247800 | A1 | 8/2019 | Ogawa et al. | |

FOREIGN PATENT DOCUMENTS

| | | | | |
|---|---|---|---|---|
| JP | 2014-204958 A | | 10/2014 | |
| JP | 2014-530643 A | | 11/2014 | |
| JP | 2015-73923 A | | 4/2015 | |
| JP | 2018-519031 A | | 7/2018 | |
| WO | WO-2008020801 A1 | * | 2/2008 | A61M 1/1696 |
| WO | WO 2009/083011 A2 | | 7/2009 | |
| WO | WO 2014/003140 A1 | | 1/2014 | |
| WO | WO 2016/191728 A1 | | 12/2016 | |
| WO | WO-2017114963 A1 | * | 7/2017 | |

OTHER PUBLICATIONS

K. Hintzen et al. "Electrodialysis and Reverse Osmosis as a Regeneration System for Hemofiltrate" Artificial Organs 7(2):169-175, Raven Press, New York 1983 International Society for Artificial Organs (Year: 1983).*

Osmonics. Osmonics Pure Water Handbook. 2nd Edition. Minnetonka, MN. 1991. Excerpt. (Year: 1991).*

Y. Yoon, R.M. Lueptow / Journal of Membrane Science 261 (2005) 76â86 (Year: 2005).*

Lenntech. Dow Water Solutions FILMTEC™ Membranes Product Information Catalog Technical Manual Excerpt, Oct. 2017 (Year: 2017).*

Crane, L. et al., "Recovery of Urea from Human Urine Using Nanofiltration and Reverse Osmosis" ACS EST Water 2023, 3, 1835-1846. https://doi.org/10.1021/acsestwater.2c00336 (Year: 2022).*

C. Courtney and D.G. Randall / Water Research 222 (2022) 118851. https://doi.org/10.1016/j.watres.2022.118851 (Year: 2022).*

Waterprofessionals. Reverse Osmosis Membranes Explained. Aug. 22, 2018. Accessed Jul. 9, 2025. https://web.archive.org/web/20180822045442/https://www.waterprofessionals.com/learning-center/reverse-osmosis-membranes-explained (Year: 2018).*

K. L McMordie Stoughton, X. Duan, and E.M. Wendel. Reverse Osmosis Optimization. U.S. Department of Energy Federal Energy Management Program. DOE/EE 0955 ■ Aug. 2013 (Year: 2013).*

Snowate. RO System Recovery Rate Calculation & Influencing Factors. https://www.snowate.com/knowledge-calculator/knowledge/ro-system-recovery-rate-analysis.html (Year: 2023).*

Indian Office Action for Indian Application No. 202147048346, dated May 10, 2022, with English translation.

Chinese Office Action and Search Report for Chinese Application No. 202080030119.7, dated Sep. 23, 2023, with an English translation.

Extended European Search Report for European Application No. 20795637.6, dated Dec. 12, 2022.

International Search Report, issued in PCT/JP2020/017821, PCT/ISA/210, dated Jun. 9, 2020.

Written Opinion of the International Searching Authority, issued in PCT/JP2020/017821, PCT/ISA/237, dated Jun. 9, 2020.

* cited by examiner

DIALYSIS SOLUTION REGENERATION METHOD

TECHNICAL FIELD

The present invention relates to a dialysate regeneration method, and more particularly to a method of separating and collecting unwanted substances such as urinary toxins contained in dialysate and regenerating the dialysate again.

BACKGROUND ART

In recent years, the number of dialysis patients has increased worldwide, and from the viewpoint of quality of life of the dialysis patients, there is a significant increase in demand for home dialysis.

In general artificial dialysis, it is necessary to use a large amount of dialysate, about 90 L to 150 L during one treatment, depending on body weight or the like. Meanwhile, since dialysate used in artificial dialysis contains waste matters such as urea moved from blood, dialysate is generally discarded after one use. Although there are devices that treat tap water and convert the tap water into dialysate, it is difficult to purify tap water into dialysis water in a region where water quality of tap water is poor. Moreover, in a region where supply of tap water is intermittent, it is difficult to treat a necessary amount of tap water for home dialysis, so it is necessary to store a large amount of dialysate for home dialysis. Further, if water stoppage continues during a disaster, dialysate cannot be produced from tap water. Therefore, there is an increasing demand for reuse of used dialysate, and several proposals have been made on techniques for regenerating used dialysate.

For example, it has been proposed to remove impurities, waste matters, and electrolyte from used dialysate by adsorbent.

Meanwhile, several kilograms of adsorbent is required for regeneration of dialysate depending on a dialysis treatment to be performed, and thus a system that minimizes weight and cost is desired.

As a method of reducing an amount of adsorbent, Patent Literature 1 proposes a system that uses an adsorbent cartridge in two stages.

Patent Literature 2 proposes a system that removes urea by urease and ion exchange resin or inorganic adsorbent.

CITATION LIST

Patent Literature

Patent Literature 1: JP-A-2014-204958
Patent Literature 2: JP-A-2014-530643

SUMMARY OF INVENTION

Technical Problem

The techniques described in Patent Literatures 1 and 2 are techniques that remove urea from used dialysate by decomposing urea into ammonia with urease and further trapping the ammonia. Therefore, in order to completely trap urea and ammonia that is a decomposition product, a plurality of types of adsorbent are required. If an amount of adsorbent is small, ammonia that is not trapped may remain, and thus a large amount of adsorbent is required. As a result, costs are increased, and a weight of a dialysate regeneration device is increased, which is not suitable for a system to be used at home.

An object of the present invention is to provide a dialysate regeneration method that has excellent urea removal performance even under a low-pressure operation and can be easily used even at home.

Solution to Problem

The present inventors have found that separation of urea can be achieved with high efficiency even under a low operating pressure by using a reverse osmosis membrane element that includes a reverse osmosis membrane having a pore diameter of 7.0 Å or less as measured by a positron annihilation lifetime measurement method, and have achieved the present invention.

In order to achieve the above object, a dialysate regeneration method of the present invention includes any of the following configurations (1) to (9).

(1) A dialysate regeneration method that reduces a urea concentration of a urea-containing aqueous solution, the method including a reverse osmosis process of obtaining, from the urea-containing aqueous solution, a concentrate having a higher urea concentration and a permeate having a lower urea concentration by using a reverse osmosis membrane element at an operating pressure of 0.5 MPa or more and 2.0 MPa or less, in which the urea concentration of the urea-containing aqueous solution is 0.5 g/L or more, the reverse osmosis membrane element includes a reverse osmosis membrane, and the reverse osmosis membrane has a pore diameter of 7.0 Å or less as measured by a positron annihilation lifetime measurement method.

(2) The dialysate regeneration method according to (1), in which a recovery rate of the permeate in the reverse osmosis process is 70% or more.

(3) The dialysate regeneration method according to (1) or (2), in which a first reverse osmosis membrane element and a second reverse osmosis membrane element are used as the reverse osmosis membrane element, and the reverse osmosis process includes:

a first step of obtaining, from the urea-containing aqueous solution, a first concentrate having a urea concentration higher than the urea concentration of the urea-containing aqueous solution and a first permeate having a urea concentration lower than the urea concentration of the urea-containing aqueous solution by the first reverse osmosis membrane element; and a second step of obtaining a second concentrate having a urea concentration higher than the urea concentration of the first concentrate and a second permeate having a urea concentration lower than the urea concentration of the urea-containing aqueous solution by the second reverse osmosis membrane element.

(4) The dialysate regeneration method according to (1) or (2), in which a first reverse osmosis membrane element and a second reverse osmosis membrane element are used as the reverse osmosis membrane element, and the reverse osmosis process includes:

a first step of obtaining, from the urea-containing aqueous solution, a first concentrate having a urea concentration higher than the urea concentration of the urea-containing aqueous solution and a first permeate having a urea concentration lower than the urea concentration of the urea-containing aqueous solution by the first reverse osmosis membrane element; and a second step of supplying the first permeate to the second reverse osmosis membrane element to obtain a second concentrate having a urea concentration higher than the urea concentration of the first permeate and a second permeate having a urea concentration lower than the urea concentration of the first permeate.

(5) The dialysate regeneration method according to any one of (1) to (4), further including a pretreatment process of reducing a salt concentration of the urea-containing aqueous solution by ion exchange before the reverse osmosis process.

(6) The dialysate regeneration method according to any one of (1) to (5), in which the reverse osmosis membrane includes:

a substrate;

a support layer located on the substrate; and a separation functional layer that is provided on the support layer and includes at least one of polyamide and cellulose acetate.

(7) The dialysate regeneration method according to any one of (1) to (6), in which all reverse osmosis membrane included in the reverse osmosis membrane element is a reverse osmosis membrane including a substrate, a support layer located on the substrate, and a separation functional layer that is provided on the support layer and includes polyamide.

(8) The dialysate regeneration method according to (7), in which in at least one of the reverse osmosis membrane element used in the reverse osmosis process, a sum of x and y calculated as described below based on amounts of amino groups, carboxy groups, and amide groups included in the separation functional layer of the reverse osmosis membrane is 0.7 or less:

x is a molar ratio of carboxy groups to amide groups as measured by $^{13}C$ solid NMR, y is a molar ratio of amino groups to amide groups as measured by $^{13}C$ solid NMR.

(9) The dialysate regeneration method according to (7) or (8), in which the separation functional layer of the reverse osmosis membrane has protrusions as folds, and when 10 arbitrary cross sections, with a length of 2.0 μm in a membrane surface direction, of the reverse osmosis membrane are observed by using an electron microscope, an average number density of the protrusions having a height of ⅕ or more of a 10-point average surface roughness of the separation functional layer is 10.0/μm or more and an average height of the protrusions is 100 nm or more in each cross section.

Advantageous Effects of Invention

The dialysate regeneration method of the present invention has excellent urea removal performance even under a low-pressure operation and can be easily used even at home. According to the dialysate regeneration method of the present invention, since dialysate can be regenerated without using a large amount of adsorbent, a cost and a weight of a dialysate regeneration device can be reduced. Further, since regeneration is possible at a low operating pressure, problems in noise and size are reduced, and thus the dialysate regeneration device can be easily used at home.

DESCRIPTION OF EMBODIMENTS

A dialysate regeneration method of the present invention includes a reverse osmosis process of obtaining, from a urea-containing aqueous solution, a concentrate having a urea concentration higher than that of the aqueous solution and a permeate having a urea concentration lower than that of the aqueous solution by using a reverse osmosis membrane element that includes a reverse osmosis membrane having a specific structure at an operating pressure of 0.5 MPa or more and 2.0 MPa or less. In the present invention, the urea-containing aqueous solution has a urea concentration of 0.5 g/L or more. It should be noted that g/L refers to a ratio of a mass of urea to a volume of the aqueous solution.

Figure 1:
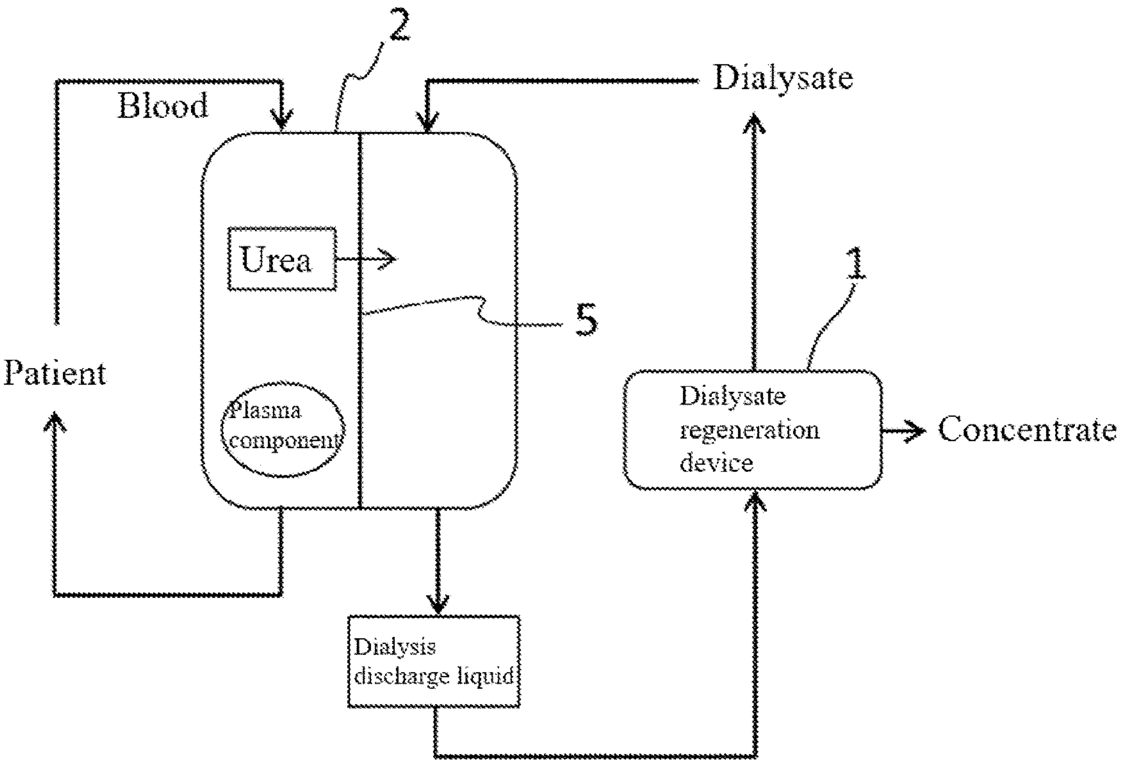
FIG. 1 is a schematic view of a dialysis system including a dialysis device and a dialysate regeneration device.

Hereinafter, a dialysate regeneration method and a dialysate regeneration device using such a method of reducing the urea concentration will be described with reference to FIGS. 1 to 3. As shown in FIG. 1, a dialysate regeneration device 1 regenerates dialysate by reducing a urea concentration of a dialysis discharge liquid. Meanwhile, the dialysate regeneration device 1 discharges a concentrate that contains urea at a higher concentration than the dialysis discharge liquid.

A known method is applied to dialysis. An outline of the dialysis will be described with reference to FIG. 1. A dialysis device 2 shown in FIG. 1 includes a dialysis membrane 5 that allows permeation of toxins such as urea and does not allow permeation of plasma components. While dialysate is supplied to a surface on one side of the dialysis membrane 5, blood is supplied to a surface on the other side. Composition of the dialysate is known, which includes sodium, potassium, calcium, magnesium, glucose, and the like. Urea in the blood diffuses into the dialysate through the dialysis membrane 5, and thus urea is removed from the blood. The dialysate that has passed through the dialysis device 2 contains urea. Such an aqueous solution is hereinafter referred to as the "dialysis discharge liquid".

In addition to urea, organic substances such as albumin, lysozyme, and glucose, and inorganic substances such as sodium chloride, sodium carbonate, calcium chloride, and potassium chloride are dissolved in the dialysis discharge liquid. Composition of the dialysis discharge liquid subjected to regeneration and concentrations of components thereof are not particularly limited.

Figure 2:
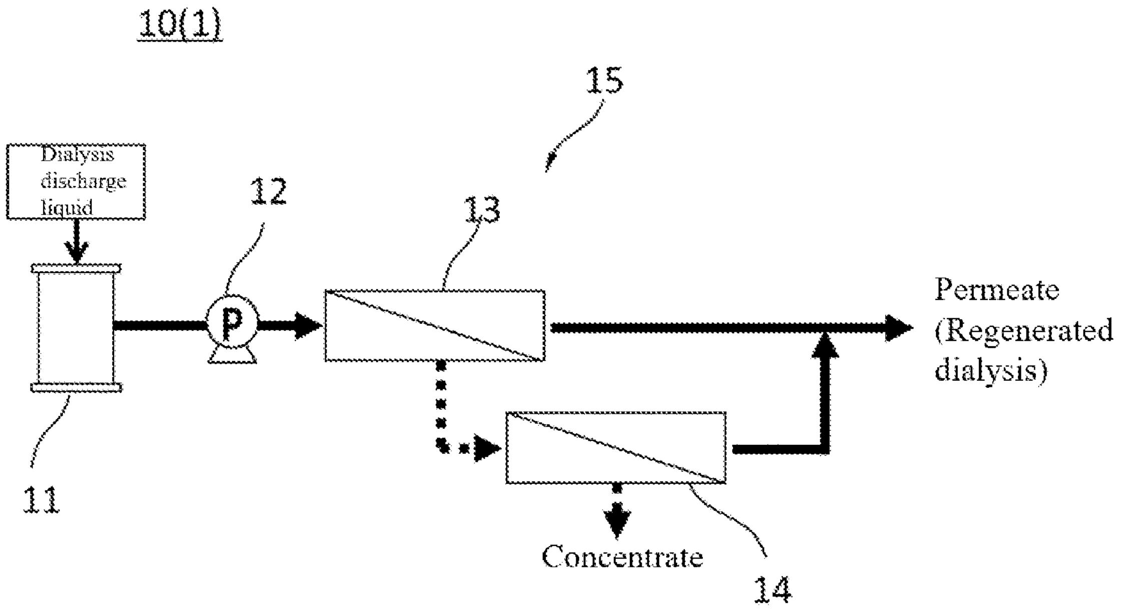
FIG. 2 is a schematic view of a dialysate regeneration device according to an embodiment of the present invention.
Figure 3:
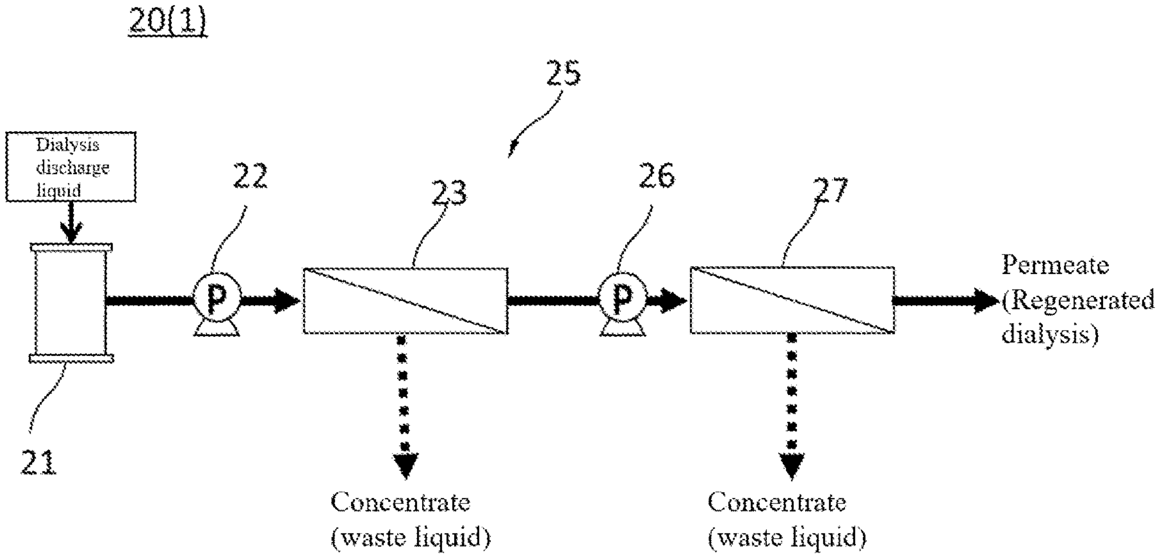
FIG. 3 is a schematic view of a dialysate regeneration device according to another embodiment of the present invention.

Dialysate regeneration devices 10 and 20 shown in FIGS. 2 and 3 and a dialysate regeneration method using the same can also deal with a dialysis discharge liquid that has a urea concentration of 0.5 g/L or more. From the viewpoint of efficiency of separation and collection, the urea concentration of the dialysis discharge liquid is preferably 10 g/L or less.

1. Dialysate Regeneration Device

FIG. 2 shows one embodiment of the dialysate regeneration device. As shown in FIG. 2, the dialysate regeneration device 10 according to a first embodiment includes a reverse osmosis device 15, and performs a reverse osmosis process by the reverse osmosis device 15. According to a dialysate regeneration method of the present embodiment, it is preferable to perform a pretreatment process of reducing a salt concentration of the urea-containing aqueous solution, that is, the dialysis discharge liquid, before performing a treatment by the reverse osmosis device 15, and the dialysate regeneration device 10 may include an ion reduction device 11 for performing the pretreatment process. As the ion reduction device 11, an ion exchange column or an electrodialyzer can be used, and it is preferable to reduce the salt concentration of the dialysis discharge liquid by ion exchange.

The ion exchange column includes a housing and ion exchange resin accommodated in the housing. The ion exchange column can remove salt from the dialysis discharge liquid. In addition, the urea concentration may be reduced due to adsorption action of the ion exchange resin.

As a salt concentration of a permeate of the ion reduction device 11, that is, a liquid to be supplied to the reverse osmosis device 15 becomes lower, pump pressure in the reverse osmosis device 15 can be reduced. The ion reduction device 11 preferably reduces the salt concentration of the dialysis discharge liquid by 80% or more.

It is not necessary to pass all of the dialysis discharge liquid through the ion reduction device, and dialysis discharge liquid passed through the ion reduction device and dialysis discharge liquid that is not passed through the ion reduction device may be mixed and then supplied to the reverse osmosis device 15. A ratio of the dialysis discharge liquid passed through the ion reduction device can be appropriately changed depending on the salt concentration or the urea concentration in the aqueous solution.

Hereinafter, a liquid supplied to the reverse osmosis device 15, particularly to a most upstream RO (reverse osmosis) membrane unit of the reverse osmosis device 15, is referred to as "raw water". The raw water is a urea-containing aqueous solution. As a range of a urea concentration of the raw water, the range described for the dialysis discharge liquid is applied. However, as described above, the salt concentration and the urea concentration may be reduced by the ion exchange resin.

It should be noted that the salt concentration in the raw water is preferably 25 g/L or less, and more preferably 20 g/L or less.

The reverse osmosis device 15 includes a supply pump 12 and a first RO (reverse osmosis) membrane unit 13 that perform the reverse osmosis process. Further, a second RO membrane unit 14 may also be provided.

The supply pump 12 is an example of a pressure adjustment device for removing urea by reverse osmosis. The supply pump 12 is arranged downstream of the ion reduction device 11 and upstream of the first RO membrane unit 13, and feeds a liquid which have been passed through the ion reduction device 11 to the first RO membrane unit 13. When the second RO membrane unit 14 is provided, a concentrate obtained from the first RO membrane unit 13 is further concentrated by the second RO membrane unit 14, as will be described later. The units are connected with a pipe.

The first RO membrane unit 13 and the second RO membrane unit 14 obtain a permeate having a reduced urea concentration and a concentrate having a high urea concentration from the raw water by reverse osmosis. Specifically, each of the first RO membrane unit 13 and the second RO membrane unit 14 includes one or a plurality of RO (reverse osmosis) membrane elements (hereinafter, simply referred to as "element"). In the present specification, an RO membrane element in the first RO membrane unit is referred to as a first RO membrane element, and an RO membrane element in the second RO membrane unit is referred to as a second RO membrane element.

FIG. 3 shows another embodiment of the dialysate regeneration device. As shown in FIG. 3, the dialysate regeneration device 20 according to a second embodiment includes a reverse osmosis device 25, and performs a reverse osmosis process by the reverse osmosis device 25. According to a dialysate regeneration method of the present embodiment, it is preferable to perform a pretreatment process of reducing the salt concentration of the dialysis discharge liquid before performing a treatment by the reverse osmosis device 25, and the dialysate regeneration device 20 may include an ion reduction device 21 for performing the pretreatment process. As the ion reduction device 21, similarly to the first embodiment, an ion exchange column or an electrodialyzer can be used, and it is preferable to reduce the salt concentration of the dialysis discharge liquid by ion exchange.

The reverse osmosis device 25 includes a first system that performs a first step of obtaining a concentrate and a permeate from the raw water, and a second system that performs a second step of further obtaining a concentrate and a permeate from the permeate obtained in the first step.

The first system includes a first supply pump 22 and a first RO (reverse osmosis) membrane unit 23. The second system includes a second supply pump 26 and a second RO membrane unit 27.

The first supply pump 22 and the second supply pump 26 are examples of the pressure adjustment device for removing urea by reverse osmosis. The first supply pump 22 is arranged downstream of the ion reduction device 21 and upstream of the first RO membrane unit 23, and feeds a liquid which have been passed through the ion reduction device 21 to the first RO membrane unit 23. The second supply pump 26 is provided on a pipe that connects a permeation side of the first RO membrane unit 23 and a supply side of the second RO membrane unit 27, and feeds a permeate of the first RO membrane unit 23 to the second RO membrane unit 27.

The first RO membrane unit 23 and the second RO membrane unit 27 obtain a permeate having a reduced urea concentration and a concentrate having a high urea concentration from the supplied liquid by reverse osmosis. Specifically, each of the first RO membrane unit 23 and the second RO membrane unit 27 includes one or a plurality of RO membrane elements (hereinafter, simply referred to as "element").

In the present embodiment, the element included in each RO membrane unit is preferably a spiral type element. The spiral type element includes, for example, a central pipe, RO membranes wound around the central pipe, and supply-side channel materials and permeation-side channel materials inserted between the RO membranes. In the spiral type element, an RO membrane, a supply-side channel material, an RO membrane, and a permeation-side channel material are repeatedly stacked in the above order. That is, supply-side channels and permeation-side channels are alternately arranged with the RO membranes interposed therebetween. One end of the spiral type element is configured to receive the supply of the dialysis discharge liquid to the supply-side channels.

Since the RO membrane does not (or does not easily) allow permeation of urea as will be described later, a urea concentration is reduced in a liquid which have been passed through the RO membrane. The permeate flows through the permeation-side channel and flows into the central pipe. A liquid that does not permeate through the RO membrane passes through a concentration-side channel as the concentrate, and is discharged from an end portion of the spiral type element.

Each of the RO membrane units 13 and 14 of the first embodiment and the RO membrane units 23 and 27 of the second embodiment includes at least one element that satisfies the following condition (I).

(I) The reverse osmosis membrane element includes a reverse osmosis membrane, and the reverse osmosis membrane has a pore diameter of 7.0 Å or less as measured by a positron annihilation lifetime measurement method.

When the pore diameter of the reverse osmosis membrane is 7.0 Å or less, separation of urea is achieved with high efficiency by a reverse osmosis treatment, and therefore, even when an operating pressure is reduced to 2.0 MPa or less, urea can be efficiently removed from raw water having a high urea concentration of 0.5 g/L or more.

In addition, when the pore diameter is 5.0 Å or more, practical water permeability can be obtained, and the dialysate can be regenerated in a short time, which is preferable from the viewpoint of using a dialysate regeneration system at home.

The positron annihilation lifetime measurement method is a method of measuring time (on an order of several hundreds of picoseconds to several tens of nanoseconds) from when a positron is incident on a sample to when the positron annihilates, and nondestructively evaluating information such as a size of a pore of 0.1 to 10 nm, a number density thereof, and distribution of the size thereof based on the annihilation lifetime. This measurement method is described in "4th Edition Experimental Chemistry Lecture", volume 14, page 485, edited by the Chemical Society of Japan, Maruzen Co., Ltd. (1992).

An average pore radius R of the separation functional layer of the reverse osmosis membrane according to the present invention is obtained from the following formula (1) based on a positron annihilation lifetime τ described above. Formula (1) shows a relationship in a case where it is assumed that o-Ps is present in a pore having a radius R in an electron layer having a thickness ΔR, and ΔR is empirically determined to be 0.166 nm (details thereof are described in Nakanishi, etc., Journal of Polymer Science, Part B: Polymer Physics, Vol. 27, p. 1419, John Wiley & Sons, Inc. (1989)).

[Formula 1]

$$\tau^{-1} = 2\left[1 - \frac{R}{R + \Delta R} + \frac{1}{2\pi}\sin\left(\frac{2\pi R}{R + \Delta R}\right)\right] \quad (1)$$

In the first embodiment, as shown in FIG. 2, the raw water is divided into a permeate (first permeate) having a lower urea concentration than the raw water and a concentrate (first concentrate) having a higher urea concentration than the raw water by the first RO membrane element of the first RO membrane unit 13 (first step). The first concentrate discharged from the first RO membrane unit 13 is discarded or supplied to a supply side of the second RO membrane unit 14 through a pipe. The first permeate obtained by the first RO membrane unit 13 is used for dialysis in the dialysis device 2 after being stored as regenerated dialysate or directly used without being stored.

When the first concentrate obtained by the first RO membrane unit 13 is supplied to the second RO membrane unit 14, a concentrate (second concentrate) and a permeate (second permeate) are obtained again by the second RO membrane element of the second RO membrane unit 14 (second step). The second concentrate is discarded, and the second permeate is used as regenerated dialysate in the same manner as the first permeate obtained in the first step.

In the second embodiment, as shown in FIG. 3, the first step is performed by the first system, in which the raw water is supplied to the first RO membrane unit 23 by the first supply pump 22, and then the first RO membrane element of the first RO membrane unit 23 divides the raw water into a permeate (first permeate) having a lower urea concentration and a concentrate (second concentrate) having a higher urea concentration.

The concentrate obtained by the first RO membrane unit 23 is discarded, and the permeate discharged from the first RO membrane unit 23 is supplied to the second RO membrane unit 27 through a pipe.

The second step is performed by the second system, in which the permeate (first permeate) of the first RO membrane unit 23 is supplied to the second RO membrane unit 27 by the second supply pump 26, and a second concentrate having a higher concentration than the permeate (first permeate) of the first RO membrane unit 23 and a second permeate having a lower urea concentration than the first permeate are obtained by the second RO membrane element of the second RO membrane unit 27. The second concentrate is discarded, and the second permeate is used for dialysis in the dialysis device 2 after being stored as regenerated permeate or directly used without being stored.

The second supply pump 26 conducts pressure adjustment for performing reverse osmosis filtration of the permeate of the first RO membrane unit 23 by the second RO membrane unit 27. An example of the second supply pump 26 is a booster pump.

It should be noted that the RO membrane unit 13 and the RO membrane unit 14 of the first embodiment and the first RO membrane unit 23 and the second RO membrane unit 27 of the second embodiment may be different from each other in configurations such as composition of RO membranes, performance of elements, structures of elements, the number of elements, and other configurations. In a case where one unit includes a plurality of elements, configurations of the elements, such as composition of RO membranes included in each element, the number of RO membranes, and structures of other members, may be different from each other.

Regardless of the number of RO membrane elements, a recovery rate of the reverse osmosis devices 15 and 25 is preferably 60% or more. That is, for the volume of the raw water supplied to the reverse osmosis devices 15 and 25, it is preferable that 60% or more can be obtained as the permeate by the urea removal system, and 40% or less is discharged as the concentrate. The recovery rate is more preferably 70% or more, and still more preferably 80% or more.

In the reverse osmosis devices 15 and 25, it is preferable that the concentrate obtained by the RO membrane element is further concentrated by another RO membrane element, and a permeate thereof is reused. As a result, even when the recovery rate of each RO membrane element (that is, a ratio of the permeate to the volume of the supplied liquid) is small, a high recovery rate can be obtained by the reverse osmosis devices 15 and 25 as a whole. That is, an amount of discarded liquid is reduced.

However, the number of RO membrane elements may be one, for example, in a case where limitation on the amount of discarded liquid is lax, or in a case where a sufficient recovery rate can be obtained by only one RO membrane element.

In addition, by concentrating the concentrate with a plurality of stages, even when a concentration rate of each RO membrane element is low (that is, even when the recovery rate is low), the pump pressure can be reduced as compared with a case where the same concentration rate is obtained by one RO membrane element. The pump pressure can be appropriately adjusted from the viewpoint of the concentration of the urea-containing aqueous solution and water permeability, and the system can be easily used at home when the pressure is in a range of 0.5 MPa or more and 2.0 MPa or less. When the pressure is 0.5 MPa or more, an appropriately high membrane permeation rate is obtained, and when the pressure is 2.0 MPa or less, a size and noise of the system can be reduced, which enables the dialysate regeneration system to be used at home. The pump pressure is more preferably 1.5 MPa or less.

When urea is concentrated stepwise by a plurality of units, pressure to the plurality of units can be supplied by one pump. However, one pump may be provided for each one unit.

A former (upstream) unit and a latter (downstream) unit are not necessarily operated at the same pressure, and a valve may be provided therebetween to change the pressure. In a case where a concentrate of the former (upstream) unit is supplied to the latter (downstream) unit, since the liquid supplied to the latter (downstream) unit has a higher concentration than the liquid supplied to the former (upstream) unit, it is preferable to increase pressure of the liquid supplied to the latter (downstream) unit. A flow rate can also be changed as appropriate.

2. Reverse Osmosis Membrane

As a membrane material of the reverse osmosis membrane element used in the present invention, a polymer material such as a cellulose acetate polymer, polyamide, sulfonated polysulfone, polyacrylonitrile, polyester, polyimide, or vinyl polymer can be used, and the membrane is not limited to be made of only one kind of such materials, and may be a membrane containing a plurality of materials. The membrane structure may be an asymmetric membrane that has a dense layer on at least a surface on one side of the membrane and has micropores having a pore diameter gradually increasing from the dense layer toward inside of the membrane or toward a surface on the other side, or a composite membrane having an extremely thin functional layer that is formed of another material on the dense layer of the asymmetric membrane. As the composite membrane, for example, a composite membrane including a support membrane made of polysulfone as a membrane material and a functional layer of polyamide as described in International Publication No. 2011/105278 can be used.

The reverse osmosis membrane used in the present invention is preferably a composite membrane that includes: a substrate; a support layer (porous support layer) that is made of a porous support membrane and located on the substrate; and a separation functional layer provided on the support layer. Especially, a composite membrane including a separation functional layer that contains at least one of cellulose acetate and polyamide is preferable, and a composite membrane including a separation functional layer that contains polyamide having higher removal performance is particularly preferable. In order to maintain durability against operating pressure, high water permeability, and rejection performance, a structure in which polyamide is used as the separation functional layer and the separation functional layer is held by a support made of a porous membrane or nonwoven fabric is suitable.

The polyamide separation functional layer preferably contains a crosslinked fully aromatic polyamide as a main component. The term "main component" refers to a component that accounts for 50% by weight or more of components of the separation functional layer. When the separation functional layer contains 50% by weight or more of the crosslinked fully aromatic polyamide, high removal performance can be exhibited. In addition, the separation functional layer is preferably formed substantially only of the crosslinked fully aromatic polyamide. A content of the crosslinked fully aromatic polyamide in the separation functional layer is preferably 80% by weight or more, and more preferably 90% by weight or more, and the separation functional layer is more preferably formed substantially only of aromatic polyamide. The phrase "the separation functional layer is formed substantially only of the crosslinked fully aromatic polyamide" means that the crosslinked fully aromatic polyamide accounts for 99% by weight or more of the separation functional layer.

The crosslinked fully aromatic polyamide can be formed by interfacial polycondensation of a polyfunctional aromatic amine and a polyfunctional aromatic acid halide. Here, it is preferable that at least one of the polyfunctional aromatic amine and the polyfunctional aromatic acid halide contains a trifunctional or higher functional compound.

Hereinafter, the separation functional layer in the present invention may be referred to as a polyamide separation functional layer.

The polyfunctional aromatic amine refers to an aromatic amine having two or more amino groups of at least one of a primary amino group and a secondary amino group in one molecule, and at least one of the amino groups is a primary amino group.

Examples of the polyfunctional aromatic amine include polyfunctional aromatic amine in which two amino groups are bonded to an aromatic ring in any of a positional relationship of an ortho position, a meta position, or a para position, such as o-phenylenediamine, m-phenylenediamine, p-phenylenediamine, o-xylylenediamine, m-xylylenediamine, p-xylylenediamine, o-diaminopyridine, m-diaminopyridine, and p-diaminopyridine, and polyfunctional aromatic amine such as 1,3,5-triaminobenzene, 1,2,4-triaminobenzene, 3,5-diaminobenzoic acid, 3-aminobenzylamine, and 4-aminobenzylamine.

In particular, m-phenylenediamine, p-phenylenediamine, and 1,3,5-triaminobenzene are preferably used in consideration of selection and separation performance, permeability, and heat resistance of the membrane. Of these, m-phenylenediamine (hereinafter also referred to as m-PDA) is more preferably used from the viewpoint of easy availability and easy handling. Such polyfunctional aromatic amines may be used alone or two or more kinds thereof may be used in combination.

The polyfunctional aromatic acid halide refers to an aromatic acid halide having at least two halogenated carbonyl groups in one molecule. Examples of trifunctional acid halides include trimesic acid chloride. Examples of bifunctional acid halides include biphenyl dicarboxylic acid dichloride, azobenzene dicarboxylic acid dichloride, terephthalic acid chloride, isophthalic acid chloride, and naphthalene dicarboxylic acid chloride. Considering reactivity with the polyfunctional aromatic amine, the polyfunctional aromatic acid halide is preferably a polyfunctional aromatic acid chloride. Considering the selection and separation performance and the heat resistance of the membrane, the polyfunctional aromatic acid halide is preferably a polyfunctional aromatic acid chloride having 2 to 4 chlorinated carbonyl groups in one molecule.

In the polyamide separation functional layer, there are amide groups derived from polymerization of the polyfunctional aromatic amine and the polyfunctional aromatic acid halide, and amino groups and carboxy groups derived from unreacted functional groups. It has been found that, when a molar ratio of carboxy groups to amide groups (carboxy groups/amide groups) in the separation functional layer is defined as x, and a molar ratio of amino groups to amide groups (amino groups/amide groups) is defined as y, if a sum of x and y (x+y) is 0.7 or less, a polymer forms a dense structure, and thus separation of urea is achieved with high efficiency and dialysate regeneration is possible even under a low pressure operation of 0.5 MPa to 2.0 MPa even in raw water having a high urea concentration of 0.5 g/L or more. When x+y is 0.3 or more, practical water permeability can be obtained, dialysate can be regenerated in a short time, which is preferable from the viewpoint of using the dialysate regeneration system at home.

The molar ratios of the carboxy groups, the amino groups, and the amide groups of the separation functional layer can be obtained by $^{13}C$ solid NMR measurement of the separation functional layer. Specifically, the substrate is peeled off from 5 $m^2$ of the reverse osmosis membrane to obtain the polyamide separation functional layer and the porous support layer, and then the porous support layer is dissolved and removed to obtain the polyamide separation functional layer. The obtained polyamide separation functional layer is measured by DD/MAS-$^{13}C$ solid NMR method, and each ratio can be calculated by comparing integral values of carbon peaks of the respective functional groups or carbon peaks where the respective functional groups are bonded.

In the polyamide separation functional layer, there are amide groups derived from polymerization of the polyfunctional aromatic amine and the polyfunctional aromatic acid halide, and amino groups and carboxy groups derived from unreacted functional groups. In addition to these, there are other functional groups included in the polyfunctional aromatic amine or the polyfunctional aromatic acid halide. Further, new functional groups can be introduced by a chemical treatment. By performing the chemical treatment, functional groups can be introduced into the polyamide separation functional layer, and thereby performance of the reverse osmosis membrane can be improved.

Examples of the new functional groups include alkyl groups, alkenyl groups, alkynyl groups, halogeno groups, hydroxyl groups, ether groups, thioether groups, ester groups, aldehyde groups, nitro groups, nitroso groups, nitrile groups, and azo groups. For example, chlorine groups can be introduced by treating with an aqueous solution of sodium hypochlorite. In addition, halogeno groups can also be introduced by a Sandmeyer reaction via formation of a diazonium salt. Further, azo groups can be introduced by performing an azo coupling reaction via formation of a diazonium salt, or phenolic hydroxyl groups can be introduced by hydrolyzing a diazonium salt.

In addition, in the separation functional layer, a thin membrane forms a fold structure that has recessed portions and protruding portions. More specifically, in the fold structure, the recessed portions and the protruding portions are repeated. Hereinafter, a recessed portion of the fold structure of the separation functional layer is referred to as a fold recessed portion or simply a recessed portion, and a protruding portion of the fold structure is referred to as a fold protruding portion or simply a protruding portion.

Figure 4:
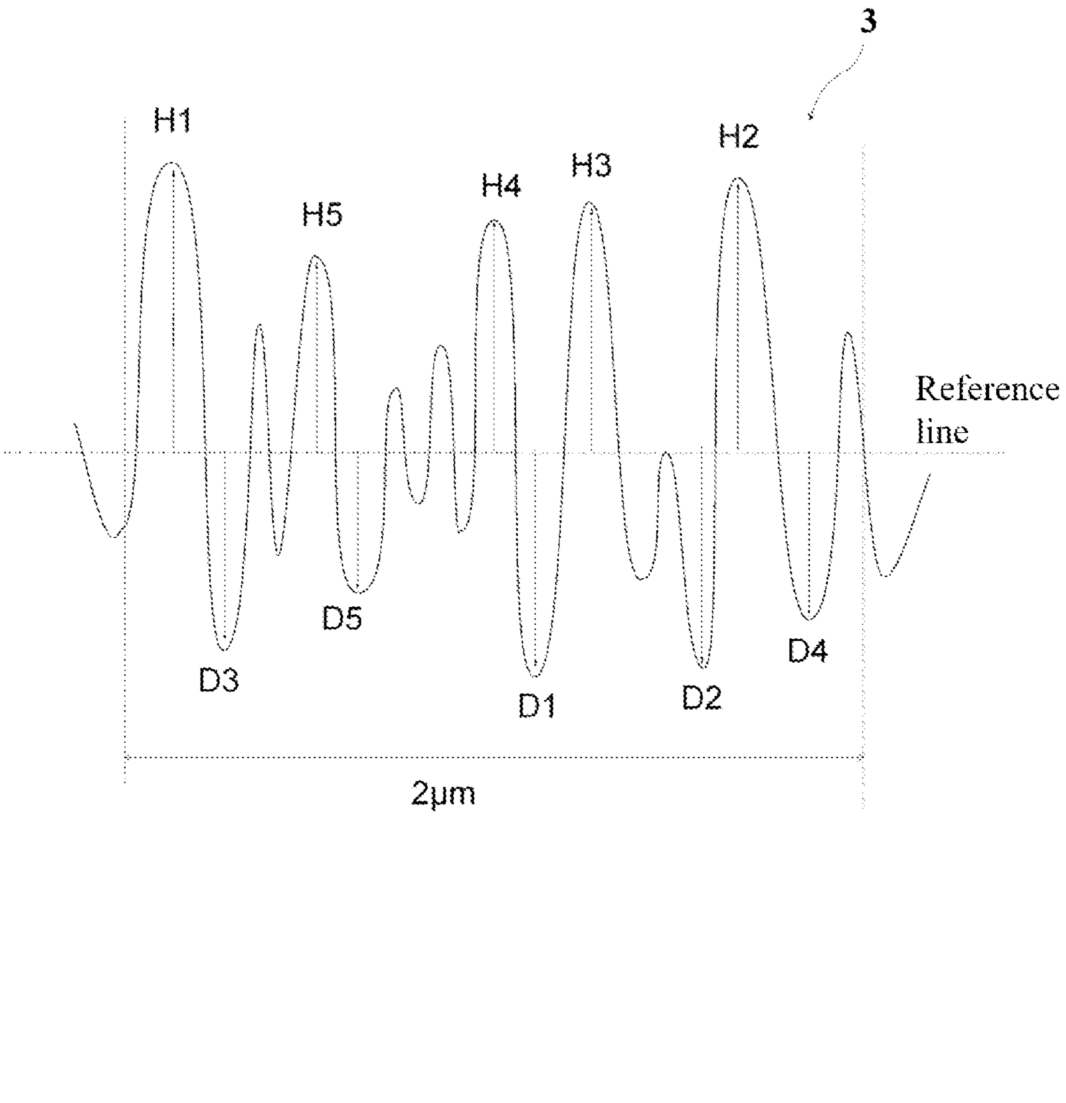
FIG. 4 schematically shows a method of measuring a height of a protruding portion of a separation functional layer.

The protruding portion of the separation functional layer in the present invention refers to a protruding portion having a height of ⅕ or more of a 10-point average surface roughness. The 10-point average surface roughness is a value obtained by the following calculation method. First, a cross section in a direction perpendicular to a membrane surface is observed by an electron microscope. An observation magnification thereof is preferably 10,000 to 100,000 times. In an obtained cross-sectional image, a surface of the separation functional layer (indicated by reference numeral "3" in FIG. 4) appears as a curve of a fold structure in which protruding portions and recessed portions are continuously repeated. A roughness curve defined based on ISO 4287: 1997 is obtained for this curve. The cross-sectional image is extracted with a width of 2.0 μm in a direction of an average line of the roughness curve.

The average line is a straight line defined based on ISO 4287: 1997, and is a straight line drawn in such a manner that a total area of a region surrounded by the average line and the roughness curve is equal above and below the average line in a measured length.

In the extracted image with a width of 2.0 μm, the height of the protruding portion and a depth of the recessed portion in the separation functional layer are measured by using the average line as a reference line. An average value of absolute values of heights H1 to H5 of five protruding portions from the highest protruding portion to a fifth highest protruding portion is calculated, an average value of absolute values of depths D1 to D5 of five recessed portions from the deepest recessed portion to a fifth deepest depth is calculated, and a sum of absolute values of the two obtained average values is calculated. The sum obtained in this manner is the 10-point average surface roughness.

The height of the protruding portion can be measured by a transmission electron microscope. First, in order to prepare an ultrathin section for the transmission electron microscope (TEM), a sample is embedded in a water-soluble polymer. As the water-soluble polymer, any water-soluble polymer may be used as long as a shape of the sample can be maintained, and for example, polyvinyl alcohol can be used. Next, in order to facilitate the observation of the cross section, the cross section is dyed with $OsO_4$, and is cut with an ultramicrotome to prepare the ultrathin section. A cross-sectional photograph of the obtained ultrathin section is taken by using the TEM.

The height of the protruding portion can be analyzed by reading the cross-sectional photograph into image analysis software. At this time, the height of the protruding portion is a value measured for a protruding portion that has a height of ⅕ or more of the 10-point average surface roughness. The height of the protruding portion is measured as follows. When cross sections at 10 arbitrary portions in the reverse osmosis membrane are observed, heights of protruding portions that are ⅕ or more of the 10-point average surface roughness described above are measured in each cross section. Here, each cross section has a width of 2.0 μm in the direction of the average line of the roughness curve.

In the present invention, the separation functional layer has protrusions as folds, and, when 10 arbitrary cross sections, whose length is 2.0 μm in a membrane surface direction, of the reverse osmosis membrane are observed by using the electron microscope, an average number density of the protrusions in each cross section, whose height is ⅕ or more of the 10-point average surface roughness of the separation functional layer, is preferably 10.0/μm or more.

When the average number density is 10.0/μm or more, the reverse osmosis membrane can obtain sufficient water permeability, and further, deformation of the protrusions at the time of pressurization can be reduced, and thus stable membrane performance can be obtained. In addition, when the average number density is 50.0/μm or less, growth of the protrusions sufficiently occurs, and a reverse osmosis membrane having desired water permeability can be easily obtained.

An average height of the protrusions of the separation functional layer in the present invention is preferably 100 nm or more, and more preferably 110 nm or more. Moreover, the average height of the protrusions of the separation functional layer is preferably 1000 nm or less, and more preferably 800 nm or less. When the average height of the protrusions is 100 nm or more, a reverse osmosis membrane having sufficient water permeability can be easily obtained. In addition, when the average height of the protrusions is 1000 nm or less, the protrusions are not crushed even when the reverse osmosis membrane is used under a high pressure operation, and thus stable membrane performance can be obtained.

3. Other Embodiments

The above-described dialysate regeneration device and the dialysate regeneration method using the same are an example of the dialysate regeneration method including the reverse osmosis process of obtaining, from the urea-containing aqueous solution, the concentrate having the higher urea concentration and the permeate having the lower urea concentration by using the reverse osmosis membrane element satisfying the condition (I).

The urea-containing solution is not limited to the dialysis discharge liquid, and composition thereof is not limited as long as urea is contained therein.

The spiral type element described as the element included in the RO membrane units 13, 14, 23, and 27 is an example of the reverse osmosis membrane element, and a form thereof can be changed to a hollow fiber membrane, a flat plate type, or the like other than the spiral type.

In the above embodiment, the reverse osmosis process includes the first step of obtaining, from the urea-containing aqueous solution, the concentrate and the permeate by the first reverse osmosis membrane element satisfying the condition (I), and a second step of obtaining, from the concentrate or the permeate obtained in the first step, the concentrate having the higher urea concentration and the permeate having the lower urea concentration than the aqueous solution subjected to the first step by the second reverse osmosis membrane element satisfying the condition (I). Although the reverse osmosis treatment is performed by using the first RO membrane units 13 and 23 in the first step and using the second RO membrane units 14 and 27 as the second step in the above embodiment, the plurality of times of reverse osmosis steps may be performed by a plurality of elements connected in one unit, that is, in one vessel. In addition, another method in which the same element is used for a plurality of times may also be adopted.

Although the pretreatment process for reducing the salt concentration of the urea-containing aqueous solution is performed before the reverse osmosis process performed by the reverse osmosis devices 15 and 25 in the above embodiment, the ion reduction devices 11 and 21 are not essential, and may be omitted if it is not necessary to reduce the salt concentration. On the other hand, salt removal by the ion reduction devices 11 and 21 may be performed at a plurality of times, or removal of salt or other solute may be performed by other means.

It is preferable that the reverse osmosis membrane element includes a reverse osmosis membrane that is a composite membrane including a substrate, a support layer located on the substrate, and a separation functional layer that is provided on the support layer and contains at least one of polyamide and cellulose acetate. It is more preferable that all of the reverse osmosis membranes included in the reverse osmosis membrane element are composite membranes each including a separation functional layer containing polyamide (polyamide-containing separation functional layer). When all of the reverse osmosis membranes include the polyamide-containing separation functional layer, separation of urea can be achieved with high efficiency even under a low operating pressure.

The dialysis and the regeneration of the dialysate may be performed in parallel, or may be performed at different timing. For example, a dialysis discharge liquid tank may be provided between the dialysis device 2 and the dialysate regeneration device 1, the dialysis discharge liquid may be stored in the tank, and the regeneration of the dialysis discharge liquid may be performed while dialysis is not performed.

EXAMPLE

Although the present invention will be described with reference to examples hereinafter, the present invention is not limited to the examples. Measurements in the examples and comparative examples are performed as follows. Hereinafter, when there is no particular description, an operation is performed at 25° C.

(Preparation of Raw Water)

As model water of dialysate, water was prepared by adding urea at 1000 mg/L and sodium chloride at 10000 mg/L to pure water. This obtained water was used as raw water A.

The raw water A was passed through a column filled with strongly acidic ion exchange resin (Amberjet (trademark) 1024, Organo Corporation), and then passed through a column filled with strongly basic ion exchange resin (Amberjet (trademark) 4002, Organo Corporation). The obtained water had a urea concentration of 520 mg/L and a sodium chloride concentration of 200 mg/L. This obtained water was used as raw water B.

(Urea Removal Rate)

Urea concentrations in a permeate and in the raw water were respectively analyzed by high performance liquid chromatography, and a removal rate was calculated by the following formula.

$$\text{Urea removal rate (\%)} = 100 \times \{1 - (\text{urea concentration in permeate}/\text{urea concentration in raw water})\}$$

(Preparation of Microporous Support Membrane)

A 16.0% by weight of DMF (dimethyl formamide) solution of polysulfone (PSf) was cast on a polyester nonwoven fabric (air permeability: 2.0 cc/cm$^2$/sec) to a thickness of 200 and immediately immersed in pure water and allowed to stand for 5 minutes so as to prepare a support membrane.

(Quantification of Carboxy Groups, Amino Groups and Amide Groups)

A substrate was physically peeled off from 5 m$^2$ of a reverse osmosis membrane, and a porous support layer and a separation functional layer were collected. After drying by allowing to stand for 24 hours, the porous support layer and the separation functional layer were added little by little to a beaker containing dichloromethane and stirred to dissolve a polymer constituting the porous support layer. Insoluble substances in the beaker were collected by filter paper. The insoluble substances were put into a beaker containing dichloromethane and stirred, and insoluble substances in the beaker were collected again. This operation was repeated until elution of the polymer forming the porous support layer cannot be detected in the dichloromethane solution. The collected separation functional layer was dried by a vacuum dryer to remove remaining dichloromethane. The obtained separation functional layer was formed into a powder sample by freeze-pulverization, sealed in a sample tube used for solid NMR measurement, and subjected to $^{13}C$ solid NMR measurement by CP/MAS method and DD/MAS method. CMX-300 manufactured by Chemagnetics Corporation was used in the $^{13}C$ solid NMR measurement. An example of measurement conditions is shown below.

Reference material: polydimethylsiloxane (internal reference: 1.56 ppm)

Sample rotation frequency: 10.5 kHz

Pulse repetition time: 100 s

Based on an obtained spectrum, peak division was performed for each peak derived from a carbon atom to which each functional group is bonded, and a ratio of an amount of functional groups is quantified based on an area of each divided peak.

(Height and Average Number Density of Fold Protruding Portion)

A reverse osmosis membrane was embedded in polyvinyl alcohol, dyed by $OsO_4$, and cut by an ultramicrotome to prepare an ultrathin section. A cross-sectional photograph of the obtained ultrathin section was taken by using a transmission electron microscope. The cross-sectional photograph taken by the transmission electron microscope was read into image analysis software, heights of fold protruding portions and depths of fold recessed portions over a length of 2.0 μm were measured, and a 10-point average surface roughness was calculated as described above. Based on the 10-point average surface roughness, heights of protruding portions that have heights of ⅕ or more of the 10-point average surface roughness were measured. Further, the number of the fold protruding portions was counted, and an average number density was obtained.

(Positron Annihilation Lifetime Measurement Method by Positron Beam Method)

A positron annihilation lifetime of a separation functional layer in each example was measured by using a positron beam method as follows. That is, the separation functional layer was dried at room temperature under reduced pressure, and cut into a 1.5 cm×1.5 cm square to obtain an inspection sample. In a positron annihilation lifetime measurement device for thin membrane equipped with a positron beam generator (this device is described in detail in, for example, Radiation Physics and Chemistry, 58, 603, Pergamon (2000)), the inspection sample is measured at a total count of 5,000,000 by a scintillation counter made of barium difluoride through using a photomultiplier tube at beam intensity of 1 keV at room temperature in vacuum, and analyzed by POSITRON FIT. An average pore diameter is calculated based on an average positron annihilation lifetime $\tau$ of a fourth component obtained by the analysis.

(Preparation of Separation Membrane A)

A 6.0% by weight aqueous solution of m-phenylenediamine was prepared. The support membrane obtained by the above operation was immersed in the above aqueous solution for 2 minutes, the support membrane was slowly pulled up in a vertical direction, blown with nitrogen from an air nozzle to remove excessive aqueous solution from a surface of the support membrane, then applied with a 45° C. decane solution containing 0.17% by weight of trimesic acid chloride (TMC) in a booth maintained at 45° C. such that the surface was completely wetted, and was allowed to stand for 10 seconds. The support membrane was placed in an oven at 140° C. and heated for 30 seconds while water vapor at 100° C. was supplied from a nozzle provided on a back surface side of the membrane so as to obtain a reverse osmosis membrane. When an amount of functional groups was analyzed, the molar ratio x of carboxy groups/amide groups was 0.35, and the molar ratio y of amino groups/amide groups was 0.32. A pore diameter measured by the positron annihilation lifetime measurement method was 5.1 Å, a fold height was 112 nm, and a fold average number density was 14.3/μm. A reverse osmosis membrane element was prepared by using this membrane.

(Preparation of Separation Membrane B)

A 2.0% by weight aqueous solution of m-phenylenediamine was prepared. The support membrane obtained by the above operation was immersed in the above aqueous solution for 2 minutes, the support membrane was slowly pulled up in a vertical direction, blown with nitrogen from an air nozzle to remove excessive aqueous solution from a surface of the support membrane, then applied with a 25° C. decane solution containing 0.12% by weight of trimesic acid chloride (TMC) in a booth maintained at 25° C. such that the surface was completely wetted, and was allowed to stand for 40 seconds so as to obtain a reverse osmosis membrane. When an amount of functional groups was analyzed, the molar ratio x of carboxy groups/amide groups was 0.60, and the molar ratio y of amino groups/amide groups was 0.48. A pore diameter measured by the positron annihilation lifetime measurement method was 6.8 Å, a fold average height was 101 nm, and a fold average number density was 15.1/μm. A reverse osmosis membrane element was prepared by using this membrane.

(Preparation of Separation Membrane C)

A 1.5% by weight aqueous solution of m-phenylenediamine was prepared. The support membrane obtained by the above operation was immersed in the above aqueous solution for 2 minutes, the support membrane was slowly pulled up in a vertical direction, blown with nitrogen from an air nozzle to remove excessive aqueous solution from a surface of the support membrane, then applied with a 25° C. decane solution containing 0.065% by weight of trimesic acid chloride (TMC) in a booth maintained at 25° C. such that the surface was completely wetted, and was allowed to stand for 60 seconds so as to obtain a reverse osmosis membrane. When an amount of functional groups was analyzed, the molar ratio x of carboxy groups/amide groups was 0.65, and the molar ratio y of amino groups/amide groups was 0.54. A pore diameter measured by the positron annihilation lifetime measurement method was 7.2 Å, a fold height was 92 nm, and a fold average number density was 17.5/μm. A reverse osmosis membrane element was prepared by using this membrane.

(Preparation of Separation Membrane D)

A cast solution obtained by mixing 25% by weight of cellulose acetate, 45% by weight of acetone, and 30% by weight of formamide was cast on the support membrane obtained by the above operation, the cast solution was evaporated for 2 minutes, and then the membrane was immersed in ice water. Next, the membrane was immersed in hot water at 90° C. so as to obtain a reverse osmosis membrane. A pore diameter thereof was 10 Å. A reverse osmosis membrane element was prepared by using this membrane.

(Preparation of Separation Membrane E)

A molar ratio of an acrylonitrile monomer and acrylic acid was adjusted to 99 mol % and 1 mol %, respectively, and polymerization is performed by a solution polymerization method under a nitrogen atmosphere using dimethyl sulfoxide as a solvent and 2,2'-azobisisobutyronitrile as a polymerization initiator so as to obtain an acrylonitrile-acrylic acid copolymer solution.

On a nonwoven fabric made of polyphenylene sulfide as a substrate, 15.0% of the acrylonitrile-acrylic acid copolymer solution was cast at 40° C. and then immediately immersed in pure water at 40° C. for 5 minutes to solidify the solution, and then immersed in hot water at 95° C. for 2 minutes to wash away dimethyl sulfoxide, thereby obtaining a porous membrane. A pore diameter thereof was 22 nm. A reverse osmosis membrane element was prepared by using this membrane.

Example 1

An operation was performed such that the raw water B was passed through the reverse osmosis membrane element prepared by using the separation membrane A at pressure of 2.0 MPa to obtain a recovery rate of 60%. An operation was performed such that an obtained concentrate was passed through the reverse osmosis membrane element prepared by using the separation membrane A to obtain a recovery rate of 50%. A recovery rate of the reverse osmosis membrane system was 80%. A urea removal rate was calculated based on an obtained permeate and found to be 82%.

Example 2

An operation was performed such that the raw water B was passed through the reverse osmosis membrane element prepared by using the separation membrane A at pressure of 1.5 MPa to obtain a recovery rate of 60%. An operation is performed such that an obtained concentrate was passed through the reverse osmosis membrane element prepared by using the separation membrane A to obtain a recovery rate of 50%. A recovery rate of the reverse osmosis membrane system was 80%. A urea removal rate was calculated based on an obtained permeate and found to be 77%.

Example 3

An operation was performed such that the raw water B was passed through the reverse osmosis membrane element prepared by using the separation membrane B at pressure of 2.0 MPa to obtain a recovery rate of 60%. An operation was performed such that an obtained concentrate was passed through the reverse osmosis membrane element prepared by using the separation membrane B to obtain a recovery rate of 50%. A recovery rate of the reverse osmosis membrane system was 80%. A urea removal rate was calculated based on an obtained permeate and found to be 69%.

Example 4

An operation was performed such that the raw water B was passed through the reverse osmosis membrane element prepared by using the separation membrane A at pressure of 1.5 MPa to obtain a recovery rate of 80%. An operation was performed such that an obtained permeate was pressurized to 0.5 MPa and passed through the reverse osmosis membrane element prepared by using the separation membrane A to obtain a recovery rate of 90%. A recovery rate of the reverse osmosis membrane system was 72%. A urea removal rate was calculated based on an obtained permeate and found to be 90%.

Example 5

An operation was performed such that the raw water A was passed through the reverse osmosis membrane element prepared by using the separation membrane B at pressure of 2.0 MPa to obtain a recovery rate of 20%. An operation was performed such that an obtained concentrate was passed through the reverse osmosis membrane element prepared by using the separation membrane B to obtain a recovery rate of 50%. A recovery rate of the reverse osmosis membrane system was 60%. A urea removal rate was calculated based on an obtained permeate and found to be 73%.

Example 6

An operation was performed such that the raw water A was passed through the reverse osmosis membrane element prepared by using the separation membrane A at pressure of 2.0 MPa to obtain a recovery rate of 50%. An operation was performed such that an obtained concentrate was passed through the reverse osmosis membrane element prepared by using the separation membrane A to obtain a recovery rate of 50%. A recovery rate of the reverse osmosis membrane system was 75%. A urea removal rate was calculated based on an obtained permeate and found to be 61%.

Example 7

An operation was performed such that the raw water B was passed through the reverse osmosis membrane element prepared by using the separation membrane A at pressure of 0.5 MPa to obtain a recovery rate of 50%. An operation was performed such that an obtained concentrate was passed through the reverse osmosis membrane element prepared by using the separation membrane A to obtain a recovery rate of 50%. A recovery rate of the reverse osmosis membrane system was 75%. A urea removal rate was calculated based on an obtained permeate and found to be 62%.

Example 8

An operation was performed such that the raw water B was passed through the reverse osmosis membrane element prepared by using the separation membrane A at pressure of 2.0 MPa to obtain a recovery rate of 70%. A urea removal rate was calculated based on an obtained permeate and found to be 75%.

Example 9

An operation was performed such that the raw water B was passed through the reverse osmosis membrane element prepared by using the separation membrane D at pressure of 2.0 MPa to obtain a recovery rate of 70%. A urea removal rate was calculated based on an obtained permeate and found to be 63%.

Comparative Example 1

An operation was performed such that the raw water B was passed through the reverse osmosis membrane element prepared by using the separation membrane C at pressure of 1.5 MPa to obtain a recovery rate of 60%. An operation was performed such that an obtained concentrate was passed through the reverse osmosis membrane element prepared by using the separation membrane C to obtain a recovery rate of 35%. A recovery rate of the reverse osmosis membrane system was 74%. A urea removal rate was calculated based on an obtained permeate and found to be 10%.

Comparative Example 2

An operation was performed such that the raw water B was passed through the reverse osmosis membrane element prepared by using the separation membrane C at pressure of 2.3 MPa to obtain a recovery rate of 50%. A urea removal rate was calculated based on an obtained permeate and found to be 30%.

Comparative Example 3

An operation was performed such that the raw water B was passed through the reverse osmosis membrane element prepared by using the separation membrane B at pressure of 0.3 MPa to obtain a recovery rate of 60%. An operation was performed such that an obtained concentrate was passed through the reverse osmosis membrane element prepared by using the separation membrane B to obtain a recovery rate of 50%. A recovery rate of the reverse osmosis membrane system was 80%. A urea removal rate was calculated based on an obtained permeate and found to be 44%.

Comparative Example 4

An operation was performed such that the raw water B was passed through the reverse osmosis membrane element prepared by using the separation membrane E at pressure of 2.0 MPa to obtain a recovery rate of 70%. A urea removal rate was calculated based on an obtained permeate and found to be 6%.

From the examples 1 to 9, it can be seen that the dialysate regeneration method of the present invention can achieve excellent urea removal performance.

Although the present invention has been described in detail using specific embodiments, it will be apparent to those skilled in the art that various modifications and variations are possible without departing from the aim and scope of the present invention. The present application is based on Japanese patent applications filed on Apr. 26, 2019, (Japanese Patent Application No. 2019-085295 and 2019-085296) and the entire thereof are incorporated by reference.

INDUSTRIAL APPLICABILITY

The present invention is suitable for regeneration of dialysate.

REFERENCE SIGNS LIST

1, 10, 20 dialysate regeneration device
2 dialysis device
3 separation functional layer
5 dialysis membrane
11 ion reduction device
12 supply pump
13 first RO (reverse osmosis) membrane unit
14 second RO membrane unit
15 reverse osmosis device
21 ion reduction device
22 first supply pump
23 first RO membrane unit
25 reverse osmosis device
26 second supply pump
27 second RO membrane unit

The invention claimed is:

1. A method of reducing a urea concentration of a urea-containing aqueous solution, the method comprising:

supplying the urea-containing aqueous solution to a reverse osmosis membrane element, and applying a pressure of 0.5 MPa or more and 2.0 MPa or less within the reverse osmosis membrane element, wherein water diffuses by reverse osmosis through a reverse osmosis membrane within the reverse osmosis membrane element, thereby separating the urea-containing aqueous solution into a concentrate having a higher urea concentration and a permeate having a lower urea concentration, thereby reducing the urea concentration of the urea-containing aqueous solution, wherein the reverse osmosis membrane comprises:

a substrate;

a support layer located on the substrate; and a separation functional layer that is provided on the support layer and comprises at least one of polyamide and cellulose acetate;

wherein the urea concentration of the urea-containing aqueous solution before said reverse osmosis is 0.5 g/L or more, wherein the reverse osmosis membrane has a pore diameter of 5.1 Å or less as measured by a positron annihilation lifetime measurement method, and wherein the reverse osmosis membrane element removes urea at a rate of 75% or more under the following concentrations and operating conditions: an aqueous solution having the urea concentration being 520 mg/L and a sodium chloride concentration of 200 mg/L is passed through the reverse osmosis membrane element at the operating pressure of 2.0 MPa at a recovery rate of the permeate of 70%.

2. The dialysate regeneration method according to claim 1, wherein the reverse osmosis membrane element comprises a first reverse osmosis membrane element and a second reverse osmosis membrane element, and the reverse osmosis process comprises:

a first step of obtaining, from the urea-containing aqueous solution, a first concentrate having a urea concentration higher than the urea concentration of the urea-containing aqueous solution and a first permeate having a urea concentration lower than the urea concentration of the urea-containing aqueous solution by the first reverse osmosis membrane element; and a second step of supplying the first concentrate to the second reverse osmosis membrane element to obtain a second concentrate having a urea concentration higher than the urea concentration of the first concentrate and a second permeate having a urea concentration lower than the urea concentration of the urea-containing aqueous solution.

3. The dialysate regeneration method according to claim 1, wherein the reverse osmosis membrane element comprises a first reverse osmosis membrane element and a second reverse osmosis membrane element, and the reverse osmosis process comprises:

a first step of obtaining, from the urea-containing aqueous solution, a first concentrate having a urea concentration higher than the urea concentration of the urea-containing aqueous solution and a first permeate having a urea concentration lower than the urea concentration of the urea-containing aqueous solution by the first reverse osmosis membrane element; and a second step of supplying the first permeate to the second reverse osmosis membrane element to obtain a second concentrate having a urea concentration higher than the urea concentration of the first permeate and a second permeate having a urea concentration lower than the urea concentration of the first permeate.

4. The dialysate regeneration method according to claim 1, further comprising a pretreatment process of reducing a salt concentration of the urea-containing aqueous solution by ion exchange before the reverse osmosis process.

5. The dialysate regeneration method according to claim 1, wherein the reverse osmosis membrane element comprises a plurality of reverse osmosis membranes, and wherein each reverse osmosis membrane is comprising the polyamide.

6. The dialysate regeneration method according to claim 5, wherein, in at least one of the reverse osmosis membrane elements used in the reverse osmosis process, a sum of x and y calculated as described below based on amounts of amino groups, carboxy groups, and amide groups included in the separation functional layer of the reverse osmosis membrane is 0.7 or less:

x is a molar ratio of carboxy groups to amide groups as measured by $^{13}C$ solid NMR, y is a molar ratio of amino groups to amide groups as measured by $^{13}C$ solid NMR.

7. The dialysate regeneration method according to claim 5, wherein the separation functional layer of the reverse osmosis membrane has protrusions as folds, and when 10 arbitrary cross sections, with a length of 2.0 μm in a membrane surface direction, of the reverse osmosis membrane are observed by using an electron microscope, an average number density of the protrusions having a height of ⅕ or more of a 10-point average surface roughness of the separation functional layer is 10.0/μm or more and an average height of the protrusions is 100 nm or more in each cross section.

8. The dialysate regeneration method according to claim 1, wherein the separation functional layer comprises 50% by weight or more of a crosslinked fully aromatic polyamide.

9. The dialysate regeneration method according to claim 8, wherein the crosslinked fully aromatic polyamide is formed by interfacial polycondensation of a polyfunctional aromatic amine and a polyfunctional aromatic acid halide, wherein the polyfunctional aromatic amine is selected from the group consisting of m-phenylenediamine, p-phenylenediamine, and 1,3,5-triaminobenzene, and wherein the polyfunctional aromatic acid halide is polyfunctional aromatic acid chloride.

10. The dialysate regeneration method according to claim 6, wherein the sum of x and y is 0.3 to 0.7.

11. The dialysate regeneration method according to claim 1, wherein the separation functional layer has recessed portions and protruding portions, wherein the protruding portions have a height of ⅕ or more of a 10-point average surface roughness.

12. The dialysate regeneration method according to claim 11, wherein an average height of protrusions of the protruding portions of the separation functional layer is 100 nm to 1000 nm.

* * * * *